(12) United States Patent
Lewis et al.

(10) Patent No.: US 10,215,658 B2
(45) Date of Patent: Feb. 26, 2019

(54) SYSTEMS, DEVICES, AND METHODS FOR DETECTING SPILLS

(71) Applicant: Walmart Apollo, LLC, Bentonville, AR (US)

(72) Inventors: Steven Jackson Lewis, Bentonville, AR (US); Matthew Dwain Biermann, Fayetteville, AR (US); Kevin Matthew Charles, Bentonville, AR (US)

(73) Assignee: Walmart Apollo, LLC, Bentonville, AR (US)

(*) Notice: Subject to any disclaimer, the term of this patent is extended or adjusted under 35 U.S.C. 154(b) by 0 days.

(21) Appl. No.: 15/730,161

(22) Filed: Oct. 11, 2017

(65) Prior Publication Data

US 2018/0100780 A1   Apr. 12, 2018

Related U.S. Application Data

(60) Provisional application No. 62/407,297, filed on Oct. 12, 2016.

(51) Int. Cl.
| | |
|---|---|
| *G01M 3/16* | (2006.01) |
| *G01N 27/12* | (2006.01) |
| *G01N 27/04* | (2006.01) |
| *G08B 21/20* | (2006.01) |
| *G08B 21/12* | (2006.01) |
| *G01M 3/00* | (2006.01) |

(52) U.S. Cl.
CPC ............... *G01M 3/16* (2013.01); *G01M 3/00* (2013.01); *G01N 27/048* (2013.01); *G01N 27/12* (2013.01); *G08B 21/12* (2013.01); *G08B 21/20* (2013.01)

(58) Field of Classification Search
CPC ........ C08L 27/16; C08L 83/04; C08L 101/12; C08K 3/04; C08K 5/19; C08K 5/41; C08K 3/22; C08K 7/24; C08K 2003/2241; C08K 2003/2272; C08K 2003/2296; C08K 2201/001; C08K 2201/011; C08K 7/00
USPC ......... 340/605, 604, 602, 539, 572.1, 573.6, 340/590–593, 601, 607, 825.49, 340/14.62–14.69
See application file for complete search history.

(56) References Cited

U.S. PATENT DOCUMENTS

| | | |
|---|---|---|
| 4,227,190 A | 10/1980 | Kelley et al. |
| H000652 H | 7/1989 | Davis et al. |
| 5,091,715 A | 2/1992 | Murphy |

(Continued)

FOREIGN PATENT DOCUMENTS

| | | |
|---|---|---|
| CA | 2837589 A1 | 6/2015 |
| JP | 2005266922 A | 9/2005 |

OTHER PUBLICATIONS

TI-5005f Floor Water Sensor, A.T. Monitors, Jan. 2006.

*Primary Examiner* — Daniel Previl
(74) *Attorney, Agent, or Firm* — McCarter & English, LLP; David R. Burns

(57) ABSTRACT

A technique for detecting spills is disclosed. A number of electrodes within a portion of a surface are connected to a resistance meter. The resistance meter detects a spill by measuring a change in resistance between two or more electrodes when a fluid is spilled over the two or more of the electrodes. The location of the spill can also be determined based on a known location for each of the electrodes. The size of the spill can further be determined based on a number of electrodes which measured a change in resistance due to the spilled fluid.

18 Claims, 6 Drawing Sheets

(56) References Cited

U.S. PATENT DOCUMENTS

| | | | |
|---|---|---|---|
| 5,272,467 A | 12/1993 | Krauleidies | |
| 5,529,567 A * | 6/1996 | Toth | B04B 7/06 494/10 |
| 5,748,092 A * | 5/1998 | Arsenault | G01M 3/18 340/602 |
| 6,620,012 B1 * | 9/2003 | Johnson | H01J 9/42 445/24 |
| 6,639,517 B1 | 10/2003 | Chapman et al. | |
| 6,683,535 B1 * | 1/2004 | Utke | G01M 3/045 200/61.04 |
| 6,846,436 B1 * | 1/2005 | Kitamura | C08K 3/04 252/511 |
| 2007/0071651 A1 * | 3/2007 | Kato | G01N 33/0052 422/83 |
| 2012/0028820 A1 | 2/2012 | Rhodes et al. | |
| 2015/0033827 A1 * | 2/2015 | Burgi | G01N 27/04 73/31.06 |
| 2016/0238547 A1 * | 8/2016 | Park | C08K 7/00 |

* cited by examiner

SYSTEMS, DEVICES, AND METHODS FOR DETECTING SPILLS

CROSS-REFERENCE TO RELATED PATENT APPLICATIONS

This application claims priority to U.S. Provisional Application No. 62/407,297 filed on Oct. 12, 2016, the content of which is hereby incorporated by reference in its entirety.

BACKGROUND

Various types of objects can fall and create spills within an enterprise, warehouse, or residence. Such objects can include, for example, liquids or hazardous chemicals.

SUMMARY

Embodiments of the present invention utilize multiple electrodes disposed within a surface to detect resistance levels associated with a fluid spill and determine the location and size of the spill. In some embodiments, the resistance values can be processed in order to identify the type of fluid spilled. In some embodiments, the location and extent of the spill can be determined based on a known location of each of the electrodes within the surface.

In one embodiment, a system for detecting spills is disclosed. The system includes a number of electrodes disposed within a portion of a surface. The system also includes a resistance meter in communication with the alternating rows of electrodes and a spill detection module executed by a processor in a processing device. The spill detection module is configured to detect a spill based on a change in a resistance value, detected by the resistance meter, between at least two of the electrodes. The spill detection module is also configured to determine a location of the spill based on a known location of each of the electrodes and to determine a size of the spill based on a number of electrodes for which a change in resistance value is detected.

In another embodiment, a method of detecting spills is disclosed that includes monitoring, using a resistance meter, a number of electrodes disposed within a portion of a surface. The method also includes detecting a spill, using a spill detection module executed by a processor in a processing device, based on a change in a resistance, detected by the resistance meter, between at least two of the electrodes. The method also includes determining a location of the spill based on a known location of each of the electrodes, and determining a size of the spill based on a number of the electrodes for which a change in resistance value is detected.

Additional combinations and/or permutations of the above examples are envisioned as being within the scope of the present disclosure. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The foregoing and other features and advantages provided by the present disclosure will be more fully understood from the following description of exemplary embodiments of the present invention when read together with the accompanying drawings, in which.

DETAILED DESCRIPTION

Figure 1:
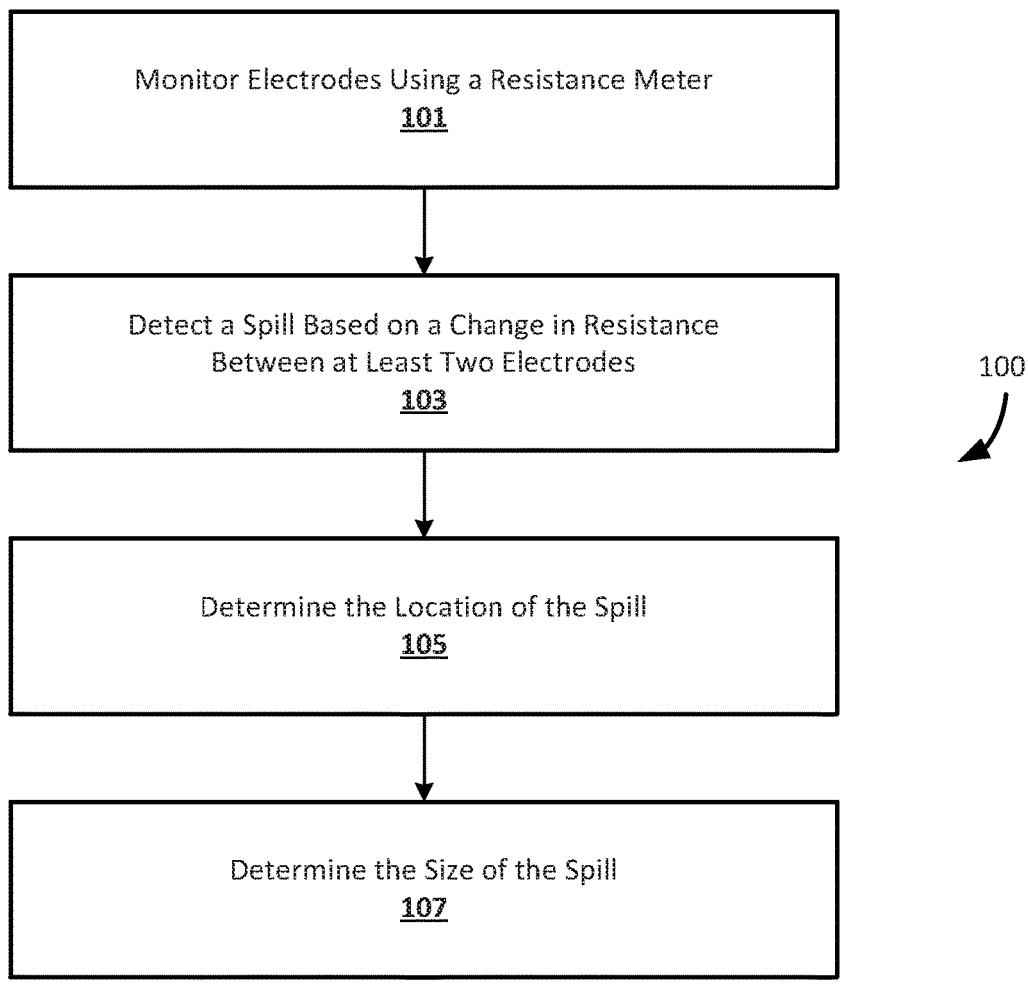
FIG. 1 is a flowchart illustrating an exemplary method for detecting spills, in accordance with an exemplary embodiment.

Following below are more detailed descriptions of various concepts related to, and embodiments of, inventive methods, devices, and systems for detecting spills. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means "includes but is not limited to", the term "including" means "including but not limited to". The term "based on" means "based at least in part on".

In accordance with some embodiments, methodologies, systems, devices, and non-transitory computer-readable media are described herein to facilitate detecting spills in a facility, which can be safety hazards for individuals near the spills. In some embodiments, a resistance meter is used to monitor the resistance between a number of electrodes that are located within a surface, such as a floor or counter space. When there is no connection between the electrodes, the resistance meter measures an infinite resistance because there is an opened circuit with no current flow. Once a fluid is spilled over the electrodes the fluid provides a pathway through which a current of electricity travels to close the circuit and thereby drop the measured resistance. This drop in resistance can be used to detect the presence of a spill and trigger an alarm that the spill should be cleaned.

In one embodiment, the location of the spill is determined based on the known location of each of the electrodes within the surface, and the size of the spill can be determined based on the number of electrodes that are in contact with the spilled fluid (i.e.: those electrodes in circuits showing a reduced resistance). A resistance threshold can be set, in some embodiments, in order to determine how sensitive the system should be determining what constitutes a "spill" and in order to prevent a spill being detected when an individual steps on two or more electrodes.

In one embodiment, a number of lighting elements can also be disposed within the surface in order to illuminate the location of the spill and facilitate finding and cleaning the spill. In an embodiment, the electrodes or portions of the floor near the spill can be raised when a spill is detected in order to provide increased traction and prevent individuals from slipping on the spilled fluid. In another embodiment, the electrodes can be lowered into the surface in order to allow the spilled fluid to drain through passageways within the surface. In still another embodiment, a portion of the surface near the spill can be heated in order to increase the evaporation rate of the spilled fluid. For example, the surface may include a heating element that can be activated when a spill is detected at or near the heating elements location by the spill detection system.

Exemplary embodiments are described below with reference to the drawings. One of ordinary skill in the art will recognize that exemplary embodiments are not limited to the illustrative embodiments, and that components of exemplary systems, devices and methods are not limited to the illustrative embodiments described below.

FIG. 1 is a flowchart illustrating a method 100 for detecting spills, in accordance with an exemplary embodiment. It will be appreciated that the method is programmatically performed by one or more computer-executable processes executing on, or in communication with, one or more computing systems or processors described further below. In step 101, a number of resistance meters are used to monitor a number of electrodes that are disposed within a portion of a surface, such as a floor or counter space. In some embodiments, the electrodes are arranged in alternating rows of electrodes, where the electrodes of each row are arranged in series. In another embodiment, the electrodes may be arranged in a different pattern to accomplish the same effect such that any spill among the pattern of electrodes would create a closed circuit for which a change in resistance level may be measured. The electrodes can be, for example, metal electrodes that are embedded into a floor such that they are flush with the floor surface but at least partially exposed to air and any fluid that may be spilled on the floor. The alternating rows of electrodes can be tied to resistance meters in such a way that if a fluid contacts two or more electrodes, a circuit is closed. When no fluid is present to make a connection between the electrodes, the resistance meters monitor the electrodes and measure the resistance as infinite, or as an open loop circuit. In some embodiments, the electrodes can be tuned to a specific resistivity so that a spill will not be detected when an individual steps on the electrodes or when a non-liquid substance contacts the electrodes.

In step 103, a processor associated with the spill detection system executes a spill detection module that detects a spill based on a change in resistance measured between at least two of the electrodes. The change in resistance can be measured, for example, using the resistance meters discussed above. As noted previously, when there is no spill present, the electrodes form an open circuit and the resistance meters measure an infinite resistance between the various electrodes embedded in the surface. However, once a spill covers more than one electrode, the liquid closes the circuit and the resistance meters measure a resistance between the electrodes.

In step 105, the location of the spill is determined based on a known location of each of the electrodes. In some embodiments, the rows of electrodes can be placed at strategic locations in the floor of an enterprise, warehouse, storage area, residence, etc., and the location of each electrode is known by the spill detection system. Once a spilled fluid creates a closed circuit between any of the electrodes as measured by the resistance meters, the system can determine the location of the spill based on the known location of the electrodes in the circuit.

In step 107, the size of the spill may be determined based on the number of electrodes for which a change in resistance is detected. In some embodiments, the spill detection system knows the location of each electrode as well as the number of electrodes between which a resistance change is detected in step 103. Accordingly, if a first fluid spill covers five electrodes and a second fluid spill covers nine electrodes, the spill detection system can determine that the second fluid spill is larger than the first fluid spill.

Figure 2:
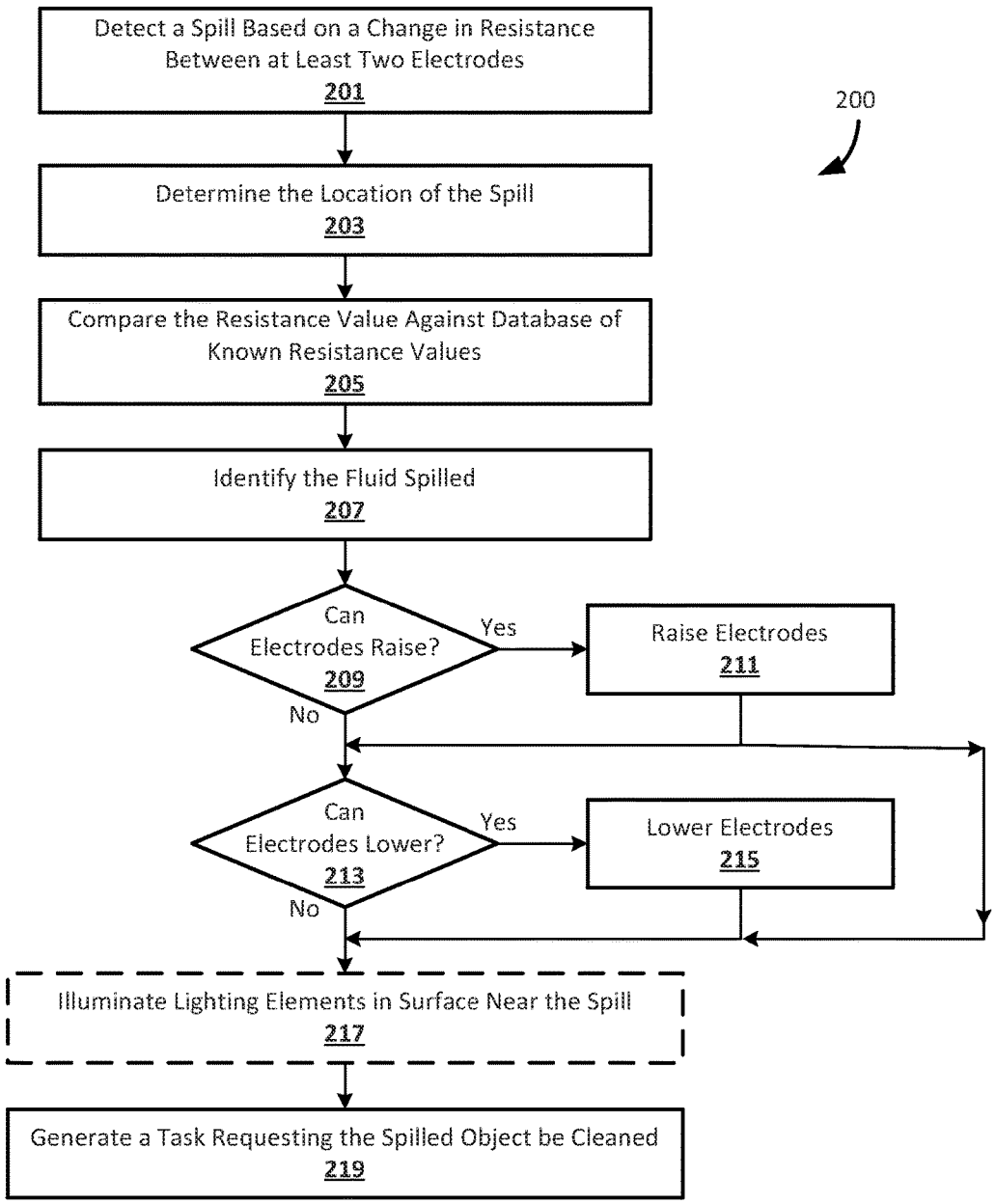
FIG. 2 is a flowchart illustrating another exemplary method for detecting spills, in accordance with an exemplary embodiment.

FIG. 2 is a flowchart illustrating another method 200 for detecting spills, in accordance with an exemplary embodiment. It will be appreciated that the method is programmatically performed by one or more computer-executable processes executing on, or in communication with, one or more computing systems or processors described further below. In some embodiments, a number of electrodes are disposed within a portion of a floor surface, and resistance meters are used to monitor the resistance between the electrodes. The electrodes can be arranged in alternating rows, for example, where the electrodes of each row are arranged in series. When no fluid is present to make a connection between the electrodes, the resistance meters monitor the electrodes and measure the resistance as infinite, or as an open loop circuit.

In step 201, a processor associated with the spill detection system executes a spill detection module that detects a spill based on a change in resistance measured between at least two of the electrodes. The change in resistance can be measured, for example, using the resistance meters discussed above. Once a spill covers more than one electrode, the liquid closes the circuit and the resistance meters measure a resistance between the electrodes, rather than an infinite resistance when there is no connection between the electrodes. In one embodiment, the spill detection system can be tuned to a specific resistivity so that a spill will not be detected when an individual steps on the electrodes or when a non-liquid substance contacts the electrodes. Further, the setting of a threshold can also allow the system to ignore trace amounts of water such as might be tracked inside a facility on an individual's shoe and deposited over one or more electrodes.

In step 203, the location of the spill is determined based on a known location of each of the electrodes. In some embodiments, the rows of electrodes can be placed at strategic locations in the floor of an enterprise, warehouse, storage area, residence, etc., and the location of each electrode is known by the spill detection system. Once a spilled fluid creates a closed circuit between any of the electrodes, the system can determine the location of the spill based on the known location of the electrodes that detected the spill.

In step 205, the spill detection module executes and compares the resistance value detected between the electrodes in step 201 against a database of known resistance values corresponding to a number of substances. Those skilled in the art will recognize that different types of fluids will create different resistance values when they connect two or more of the electrodes. For example, if water spills and creates a closed circuit between two of the electrodes, the resistance measured by the resistance meters will be different than if oil or detergent had spilled. In one embodiment, a database of known resistance values corresponding to a number of substances can be compared against the resistance value measured in step 201. The number of known resistance values in the database searched in this comparison can be limited, in one embodiment, by the location determined in step 203. For example, if a spill is detected in the produce section of a store, the resistance value detected in step 201 can be first or only compared against the known resistance values of objects typically located in that area of the store.

In step 207, the spill detection module executes and identifies the type of fluid spilled based on a match found in the comparison of step 205. In some embodiments, the resistance value detected in step 201 between at least two of the electrodes will match one of the known resistance values in the database of known resistance values. When such a match is found, the spill detection module can identify the type of fluid spilled. This identification can facilitate cleaning of the spill.

In step 209, the spill detection system determines whether the electrodes can raise such that they protrude above the surface. If the electrodes can be raised, the method continues to step 211 where an electrode movement module is executed by the processor and one or more of the electrodes is raised such that a portion of the electrode protrudes above the surface within which the electrodes are disposed. For example, if a spill is detected on the floor of a warehouse, the electrodes involved in the spill can be raised slightly above the surface of the floor in order to provide increased traction and prevent slips that may result from a fluid spill.

After the electrodes are raised in step 211, or after it is determined in step 209 that the electrodes cannot be raised, the method continues with step 213 where the spill detection system determines whether the electrodes can lower within the surface. If the electrodes can be lowered, the method continues to step 215 where a spill drain module is executed by the processor and one or more of the electrodes involved in the spill is lowered within a passageway in the surface. Once the electrodes are lowered, the fluid spilled can drain through the passageways. It should be appreciated that the spill detection system may also be implemented in some embodiments so that the electrodes raise or lower but do not perform both functions.

In step 217, in one embodiment in which the spill detection system is equipped with lighting elements disposed in the surface, the processor executes an illumination module to illuminate one or more of the lighting elements that are at or near the location of the spill, determined in step 203, or that can otherwise indicate the location of the spill.

In step 219, the processor executes a notification module to generate a task requesting that the surface upon which the spill is detected be cleaned. For example, in one embodiment, the spill detection system may include a transmitter and the notification may be wirelessly transmitted to a mobile device operated by an individual assigned the task of cleaning up the spill. In some embodiments, the priority of the task is determined based on the identity of the fluid, determined in step 207, or the size of the spill. For example, if a spill of orange juice and a spill of a detergent are both detected, the notification module may assign a higher priority to the detergent spill because it causes a greater health hazard than a spill of orange juice. Once a spill is cleaned, an individual can acknowledge that the task has been completed and reset the system, in some embodiments.

Figure 3:
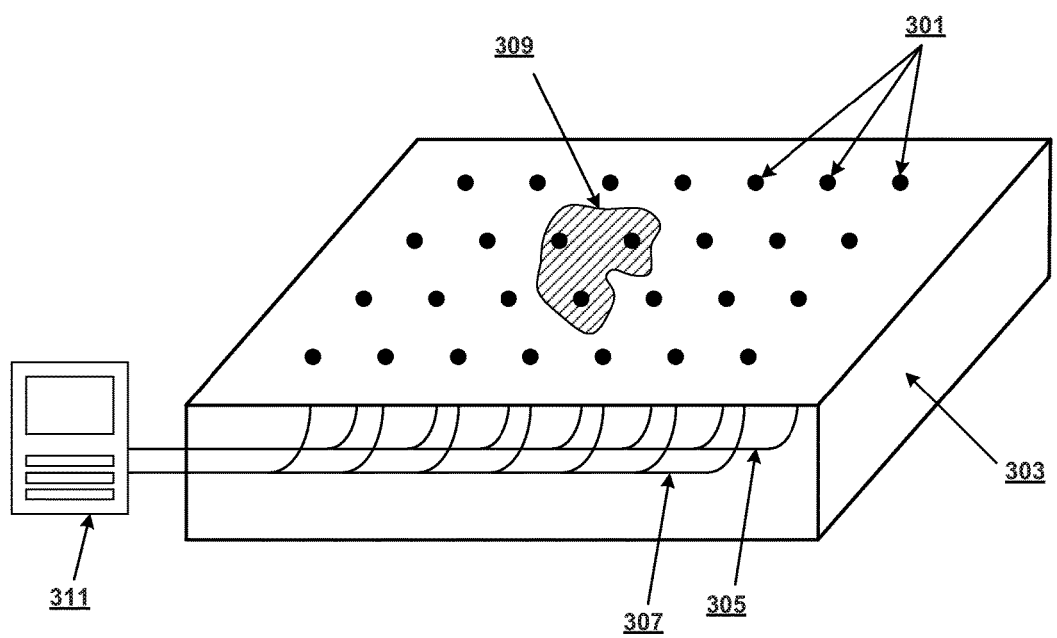
FIG. 3 illustrates a perspective cross-sectional view of a portion of floor with a number of electrodes disposed therein, in accordance with an exemplary embodiment.

FIG. 3 illustrates a perspective cross-sectional view of a portion of floor 303 with a number of electrodes 301 disposed therein, in accordance with an exemplary embodiment. In this example embodiment, four rows of electrodes 301 are disposed within the floor 303, and the electrodes in each row are connected in series using electrode connections 305, 307. The arrangements of the electrodes may form a number of different types of patterns. For example, without limitation, in one embodiment, a positive terminal in a row may be located across from a negative terminal in the next row. Similarly, a positive terminal may instead, or in addition, be located adjacent to a negative terminal in the same row of electrodes. These electrode connections 305, 307 can create an electrical connection between the electrodes 301 and a centralized system 311, which includes a number of resistance meters that can measure the resistance values between the electrodes. In some embodiments, a network of resistance meters can be controlled centrally by the centralized system 311. When a fluid spill 309 occurs, the resistance between the electrodes 301 covered by the spill 309 can be detected and measured by the resistance meters associated with the system 311 in order to detect the spill 309. In some embodiments, because each resistance meter is connected to the centralized system 311, the system 311 can determine which electrodes are exposed to the spill 309 based on which resistance meters are registering the resistivity between the electrodes 301.

In exemplary embodiments, each of the electrodes 301 is initially flush with the upper surface of the floor 303, with a portion of each electrode exposed to air or any fluid spilled on the floor. The electrodes could be metal electrodes, in some embodiments, that the spill detection system may tune to a specific resistivity such that a spill will only be detected when a fluid covers more than one electrode, rather than when an individual steps on the electrodes. In some embodiments, once a spill is detected, the electrodes 301 exposed to the spill 309 can raise, as described above, in order to provide increased traction to individuals walking on the floor 303. In other embodiments, the electrodes 301 exposed to the spill 309 can lower in order to allow the fluid to drain through passageways in the floor 303.

Figure 4:
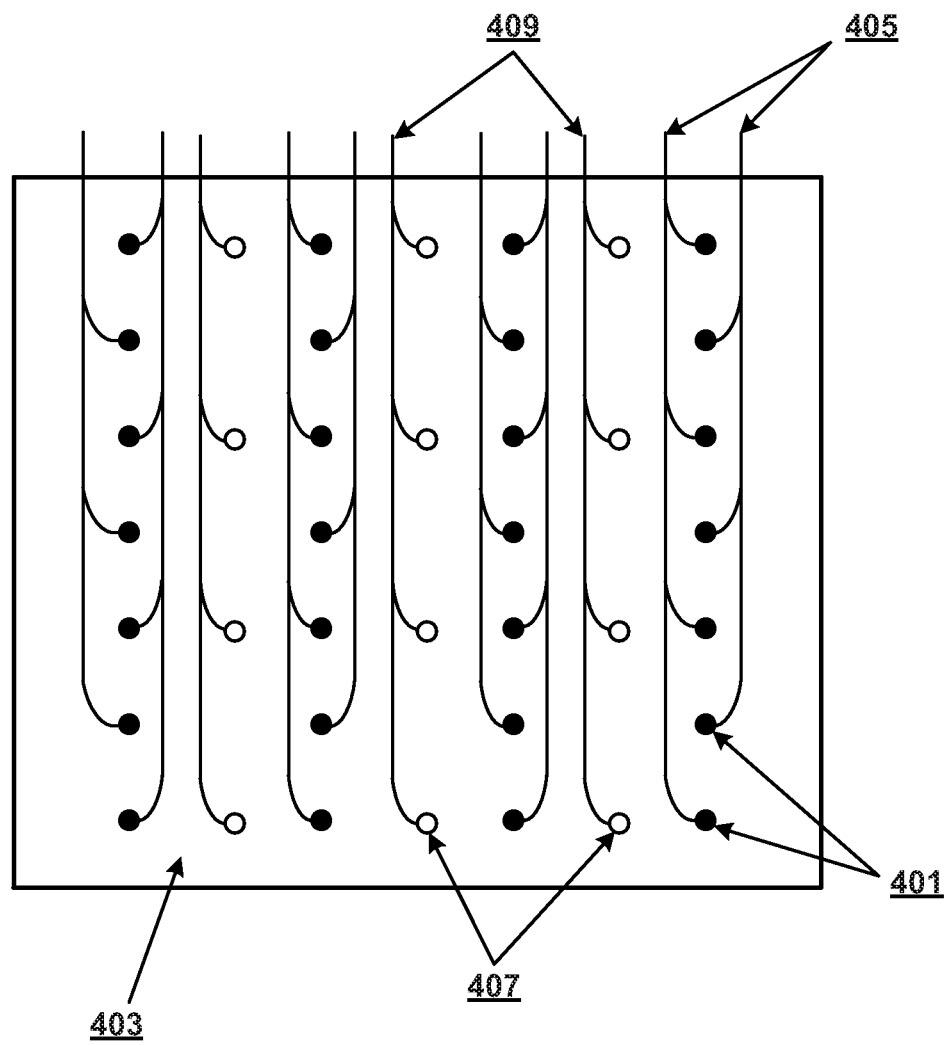
FIG. 4 illustrates a view from above of a portion of floor with a number of electrodes disposed therein, in accordance with an exemplary embodiment.

FIG. 4 illustrates a view from above of a portion of floor 403 with a number of electrodes 401 disposed therein, in accordance with an exemplary embodiment. In this example embodiment, eight rows 405 of electrodes 401 are disposed within the floor 403 with a portion of each electrode 401 exposed to the air. In some embodiments, the polarity of the rows 405 of electrodes 401 is arranged such that a closed circuit will be created when a fluid spills over two adjacent electrodes 401. The rows 405 of electrodes can be in electrical communication with a number of resistance meters (not shown) as described above in order to monitor the resistance between the electrodes 401. In this example embodiment, a number of lighting elements 407 are also disposed within the floor 403. These lighting elements 407 can include, for example, strings 409 of LEDs that can be configured to illuminate an area associated with or proximal to a detected fluid spill, as described above. In some embodiments, lighting elements 407 in the floor 403 can indicate the location of a fluid spill or lead an individual to the location of a fluid spill.

Figure 5:
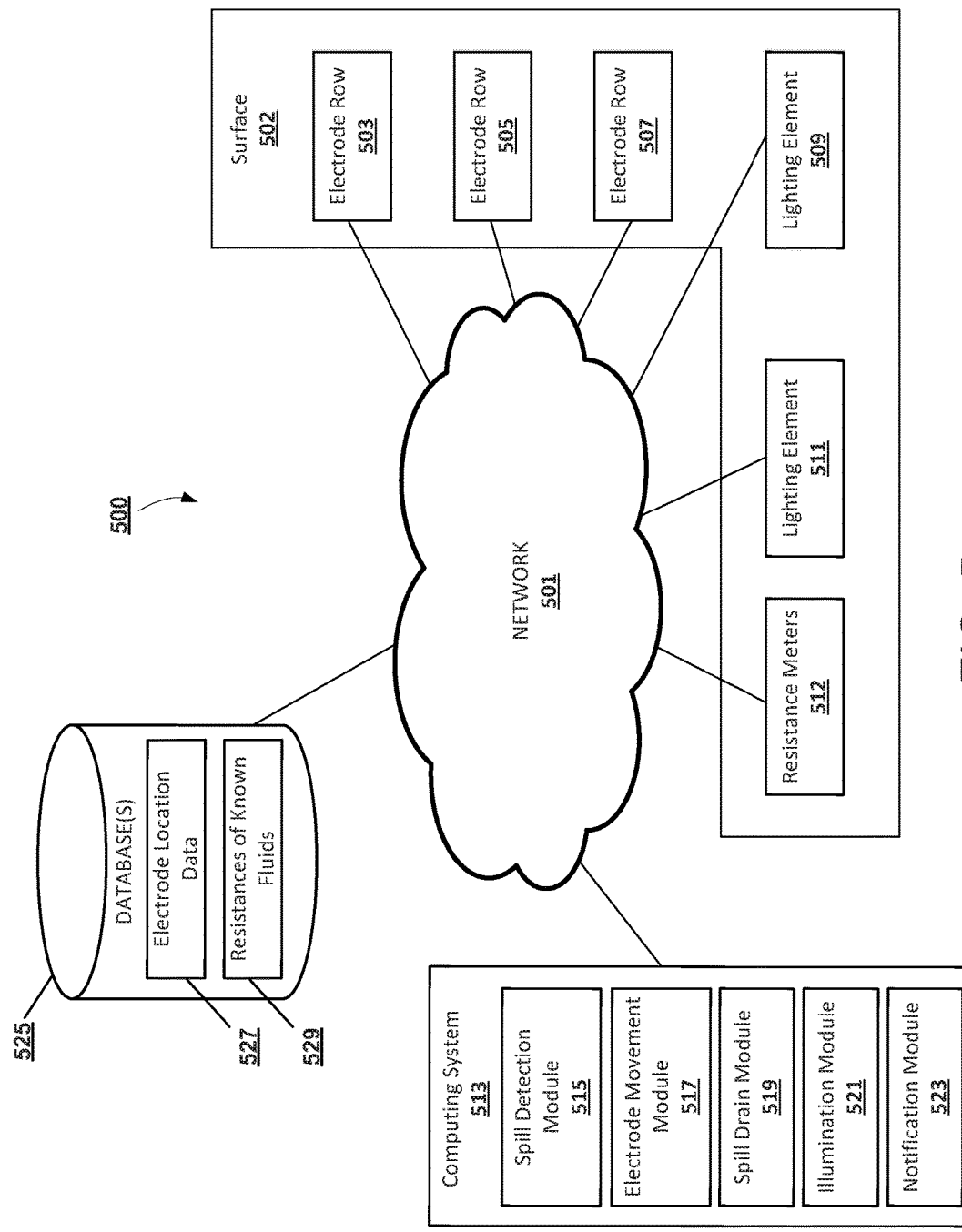
FIG. 5 is a diagram of an exemplary network environment suitable for a distributed implementation of an exemplary embodiment.

FIG. 5 illustrates a network diagram depicting a system 500 suitable for a distributed implementation of exemplary embodiments. The system 500 can include a network 501. The system 500 can also include, disposed in a floor surface 502 of a physical facility such as a floor, a number of rows of electrodes 503, 505, 507 and a number of lighting elements 509, 511. The system 500 may also include resistance meters 512, a computing system 513, and a database 525. As will be appreciated, various distributed or centralized configurations may be implemented. In exemplary embodiments, the computing system 513 can store a spill detection module 515, an electrode movement module 517, a spill drain module 519, an illumination module 521, and a notification module 523, which can implement one or more of the processes described herein with reference to FIGS. 1-2, or portions thereof. It will be appreciated that the module functionality may be combined or divided as a greater or lesser number of modules than illustrated, and that the same computing system or server could host one or more modules. The database 525 can store the electrode location data 527 and the resistances of known fluids 529, in exemplary embodiments.

The resistance meters 512, computing system 513, electrode rows 503, 505, 507, lighting elements 509, 511, and the database 525 may connect to the network 501 and be in communication with each other via a wired or wireless connection, in some embodiments. In some embodiments, the computing system 513 can communicate with the resistance meters 512, and/or electrode rows 503, 505, 507 in order to receive resistance data relating to a spill incident, as described above. The computing system 513 may include one or more applications such as, but not limited to, a web browser, a sales transaction application, an object reader application, and the like. The computing system 513 may include some or all components described in relation to computing device 600 shown in FIG. 6.

The communication network 501 may include, but is not limited to, the Internet, an intranet, a LAN (Local Area Network), a WAN (Wide Area Network), a MAN (Metropolitan Area Network), a wireless network, an optical network, and the like. In some embodiments, the resistance meters 512, computing system 513, electrode rows 503, 505, 507, lighting elements 509, 511, and the database 525 can transmit instructions to each other over the communication network 501. In exemplary embodiments, the electrode location data 527 and the resistances of known fluids 529 can be stored at the database 525 and received at the computing system 513 in response to a service performed by a database retrieval application.

Figure 6:
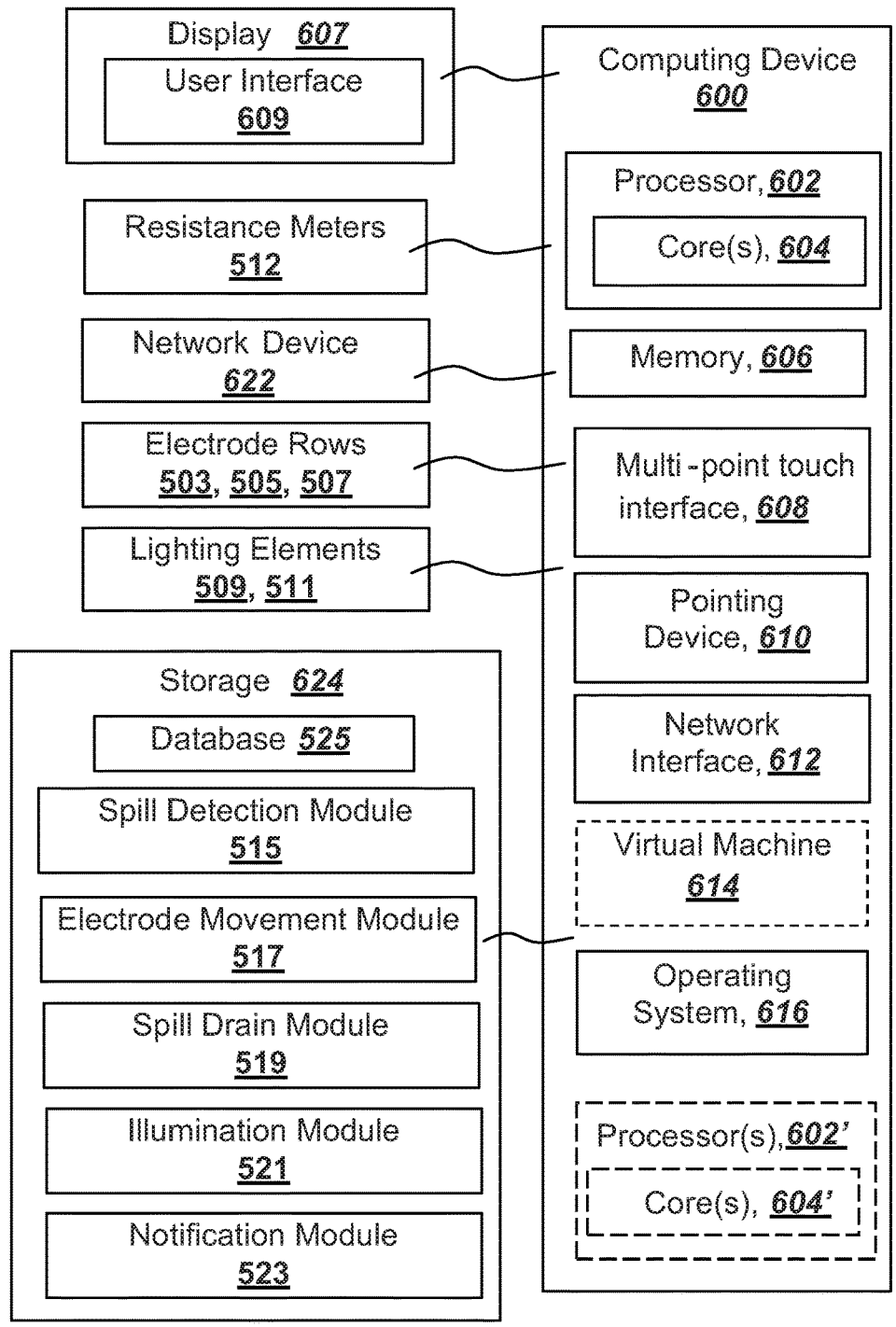
FIG. 6 is a block diagram of an exemplary computing device that can be used to perform exemplary processes in accordance with an exemplary embodiment.

FIG. 6 is a block diagram of an exemplary computing device 600 that can be used in the performance of any of the example methods according to the principles described herein. The computing device 600 includes one or more non-transitory computer-readable media for storing one or more computer-executable instructions (such as but not limited to software or firmware) for implementing any example method according to the principles described herein. The non-transitory computer-readable media can include, but are not limited to, one or more types of hardware memory, non-transitory tangible media (for example, one or more magnetic storage disks, one or more optical disks, one or more USB flashdrives), and the like.

For example, memory 606 included in the computing device 600 can store computer-readable and computer-executable instructions or software for implementing exemplary embodiments performing processes described above in reference to FIGS. 1-2. The computing device 600 also includes processor 602 and associated core 604, and optionally, one or more additional processor(s) 602' and associated core(s) 604' (for example, in the case of computer systems having multiple processors/cores), for executing computer-readable and computer-executable instructions or software stored in the memory 606 and other programs for controlling system hardware. Processor 602 and processor(s) 602' can each be a single core processor or multiple core (604 and 604') processor.

Virtualization can be employed in the computing device 600 so that infrastructure and resources in the computing device can be shared dynamically. A virtual machine 614 can be provided to handle a process running on multiple processors so that the process appears to be using only one computing resource rather than multiple computing resources. Multiple virtual machines can also be used with one processor.

Memory 606 can be non-transitory computer-readable media including a computer system memory or random access memory, such as DRAM, SRAM, EDO RAM, and the like. Memory 606 can include other types of memory as well, or combinations thereof.

A user can interact with the computing device 600 through a display 607, such as an e-paper display, a LED display, an OLED display, a LCD, a touch screen display, or computer monitor, which can display one or more user interfaces 609 that can be provided in accordance with exemplary embodiments. The computing device 600 can also include other I/O devices for receiving input from a user, for example, a keyboard or any suitable multi-point touch interface 608, a pointing device 610 (e.g., a pen, stylus, mouse, or trackpad). The multi-point touch interface 608 and the pointing device 610 can be coupled to the display 607. The computing device 600 can include other suitable conventional I/O peripherals.

The computing device 600 can also be in communication with one or more rows of electrodes 503, 505, 507, one or more lighting elements 509, 511 and resistance meters 512. As discussed above, each row of electrodes 503, 505, 507 can include a number of electrodes arranged in series and connected to resistance meters 512 to measure the resistance between the electrodes, and the lighting elements 509, 511 can include LEDs or other light sources configured to illuminate a location associated with the spill, as described above.

The computing device 600 can also include one or more storage devices 624, such as a hard-drive, CD-ROM, or other non-transitory computer readable media, for storing data and computer-readable instructions and/or software, such as a spill detection module 515, an electrode movement module 517, a spill drain module 519, an illumination module 521, and a notification module 523 that can implement exemplary embodiments of the methods and systems as taught herein, or portions thereof. Exemplary storage device 624 can also store one or more databases 525 for storing any suitable information required to implement exemplary embodiments. The databases 525 can be updated by a user or automatically at any suitable time to add, delete, or update one or more items in the databases. Exemplary storage device 624 can store one or more databases 525 for storing the electrode location data 527, resistances of known fluids 529, and any other data/information used to implement exemplary embodiments of the systems and methods described herein.

The computing device 600 can include a network interface 612 configured to interface via one or more network devices 622 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 612 can include a built-in network adapter, network interface card, PCMCIA network card, card bus network adapter, wireless network adapter, USB network adapter, modem or any other device suitable for interfacing the computing device 600 to any type of network capable of communication and performing the operations described herein. Moreover, the computing device 600 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The computing device 600 can run operating system 616, such as versions of the Microsoft® Windows® operating systems, different releases of the Unix and Linux operating systems, versions of the MacOS® for Macintosh computers, embedded operating systems, real-time operating systems, open source operating systems, proprietary operating systems, operating systems for mobile computing devices, or any other operating system capable of running on the computing device and performing the operations described herein. In exemplary embodiments, the operating system 616 can be run in native mode or emulated mode. In an exemplary embodiment, the operating system 616 can be run on one or more cloud machine instances.

In describing example embodiments, specific terminology is used for the sake of clarity. For purposes of description, each specific term is intended to at least include all technical and functional equivalents that operate in a similar manner to accomplish a similar purpose. Additionally, in some instances where a particular example embodiment includes system elements, device components or method steps, those elements, components or steps can be replaced with a single element, component or step. Likewise, a single element, component or step can be replaced with multiple elements, components or steps that serve the same purpose. Moreover, while example embodiments have been shown and described with references to particular embodiments thereof, those of ordinary skill in the art will understand that various substitutions and alterations in form and detail can be made therein without departing from the scope of the disclosure. Further still, other aspects, functions and advantages are also within the scope of the disclosure.

Example flowcharts are provided herein for illustrative purposes and are non-limiting examples of methods. One of ordinary skill in the art will recognize that example methods can include more or fewer steps than those illustrated in the example flowcharts, and that the steps in the example flowcharts can be performed in a different order than the order shown in the illustrative flowcharts.

What is claimed is:

1. A system for detecting spills comprising:
   a plurality of electrodes disposed within a portion of a surface;
   a resistance meter in communication with the plurality of rows of electrodes; and
   a spill detection module executed by a processor in a processing device and in communication with a database, the spill detection module configured to:
   detect a spill based on a change in a resistance value between at least two electrodes among the plurality of electrodes, the change detected by the resistance meter;
   determine a location of the spill based on a known location of each of the plurality of electrodes;
   determine a size of the spill based on a number of the at least two electrodes for which a change in resistance value is detected;
   retrieve known resistance values from the database corresponding to a plurality of substances;
   compare the resistance value detected between the at least two of the plurality of electrodes against the retrieved resistance values corresponding to the plurality of substances; and
   identify a type of fluid spilled based on a comparison of the resistance value detected between the at least two of the plurality of electrodes and the retrieved resistance values corresponding to the plurality of substances.

2. The system of claim 1 wherein the plurality of electrodes are arranged in alternating rows of electrodes.

3. The system of claim 1, further comprising an electrode movement module executed by the processor, the electrode movement module configured to:
   raise at least one of the electrodes, in response to detecting the spill, such that at least a portion of the at least one electrode protrudes above the surface within which the plurality of electrodes are disposed.

4. The system of claim 1, further comprising a spill drain module executed by the processor, the spill drain module configured to:
   lower at least one of the plurality of electrodes within a passageway in the surface, in response to detecting the spill, such that a fluid spilled can drain through the passageway in the surface.

5. The system of claim 1, further comprising:
   a plurality of lighting elements disposed within the surface; and
   an illumination module executed by the processor and configured to illuminate lighting elements to reflect the determined location of the spill.

6. The system of claim 1, further comprising a notification module executed by the processor, the notification module configured to:
   generate a task requesting that the fluid spilled be cleaned.

7. The system of claim 6, wherein a priority of the task is determined based on at least one of an identity of the fluid spilled and the size of the spill.

8. A method for detecting spills comprising:
   monitoring, using a resistance meter, a plurality of electrodes disposed within a portion of a surface;
   detecting a spill, using a spill detection module executed by a processor in a processing device and in communication with a database, based on a change in a resistance value between at least two electrodes among the plurality of electrodes, the change detected by the resistance meter;
   determining a location of the spill based on a known location of each of the plurality of electrodes; and
   determining a size of the spill based on a number of the at least two electrodes for which a change in resistance value is detected;
   retrieving known resistance values from the database corresponding to a plurality of substances;
   comparing the resistance value detected between the at least two of the plurality of electrodes against the retrieved resistance values corresponding to the plurality of substances; and
   identifying a type of fluid spilled based on a comparison of the resistance value detected between the at least two of the plurality of electrodes and the retrieved resistance values corresponding to the plurality of substances.

9. The method of claim 8, further comprising:
raising at least one of the plurality of electrodes in response to detecting the spill, using an electrode movement module executed by the processor, such that at least a portion of the at least one electrode protrudes above the surface within which the plurality of electrodes are disposed.

10. The method of claim 8, further comprising:
lowering at least one of the electrodes within a passageway in the surface in response to detecting the spill, using a spill drain module executed by the processor, such that a fluid spilled can drain through the passageway in the surface.

11. The method of claim 8, further comprising:
illuminating one or more lighting elements disposed within the surface to reflect the determined location of the spill, using an illumination module executed by the processor, in response to detecting the spill.

12. The method of claim 8, further comprising:
generating a task, using a notification module executed by the processor, requesting that a fluid spilled be cleaned.

13. The method of claim 12, wherein a priority of the task is determined based on an identity of the fluid spilled.

14. A non-transitory machine readable medium storing instructions for detecting spills executable by a processing device, wherein execution of the instructions causes the processing device to:
monitor a plurality of electrodes disposed within a portion of a surface;
detect a spill based on a change in resistance value between at least two electrodes among the plurality of electrodes, the change detected by the resistance meter;
determine a location of the spill based on a known location of each of the plurality of electrodes;
determine a size of the spill based on a number of the at least two electrodes for which a change in resistance value is detected;
retrieve known resistance values from a database, corresponding to a plurality of substances;
compare the resistance value detected between the at least two of the plurality of electrodes against the retrieved resistance values corresponding to the plurality of substances; and
identify a type of fluid spilled based on a comparison of the resistance value detected between the at least two of the plurality of electrodes and the retrieved resistance values corresponding to the plurality of substances.

15. The non-transitory machine readable medium of claim 14, wherein execution of the instructions further causes the processing device to:
execute an electrode movement module to raise at least one of the electrodes in response to detecting the spill such that at least a portion of the at least one electrode protrudes above the surface within which the plurality of electrodes are disposed.

16. The non-transitory machine readable medium of claim 14, wherein execution of the instructions further causes the processing device to:
execute an illumination module in response to detecting the spill to illuminate one or more lighting elements disposed within the surface to reflect the determined location of the spill.

17. The non-transitory machine readable medium of claim 14, wherein execution of the instructions further causes the processing device to:
execute a notification module to generate a task requesting that the fluid spilled be cleaned, wherein a priority of the task is determined based on an identity of the fluid spilled.

18. The non-transitory machine readable medium of claim 14, wherein execution of the instructions further causes the processing device to:
lower at least one of the plurality of electrodes within a passageway in the surface in response to detecting the spill, using a spill drain module executed by the processor, such that a fluid spilled can drain through the passageway in the surface.

* * * * *